United States Patent
Sakaguchi

(10) Patent No.: US 9,182,380 B2
(45) Date of Patent: Nov. 10, 2015

(54) SIGNAL PROCESSING APPARATUS, SIGNAL PROCESSING SYSTEM, PROBE, SIGNAL PROCESSING METHOD, AND PROGRAM

(75) Inventor: Tatsumi Sakaguchi, Kanagawa (JP)

(73) Assignee: Sony Corporation, Tokyo (JP)

(*) Notice: Subject to any disclaimer, the term of this patent is extended or adjusted under 35 U.S.C. 154(b) by 530 days.

(21) Appl. No.: 13/459,400

(22) Filed: Apr. 30, 2012

(65) Prior Publication Data

US 2012/0300578 A1    Nov. 29, 2012

(30) Foreign Application Priority Data

May 24, 2011    (JP) .................................. 2011-115880

(51) Int. Cl.
*G01N 29/26*    (2006.01)
(52) U.S. Cl.
CPC ..................................... *G01N 29/262* (2013.01)
(58) Field of Classification Search
CPC .................................. G03B 42/06; H04B 1/02
USPC ..................... 73/602, 622, 625; 600/443, 447
See application file for complete search history.

(56) References Cited

U.S. PATENT DOCUMENTS

| | | | | |
|---|---|---|---|---|
| 4,752,896 | A | * | 6/1988 | Matsumoto .................... 600/437 |
| 5,078,145 | A | * | 1/1992 | Furuhata ........................ 600/443 |
| 5,435,311 | A | | 7/1995 | Umemura et al. |
| 5,974,891 | A | * | 11/1999 | Uchikawa et al. .............. 73/625 |
| 6,045,508 | A | | 4/2000 | Hossack et al. |
| 7,455,641 | B2 | * | 11/2008 | Yamada et al. ................ 600/437 |
| 7,632,233 | B2 | * | 12/2009 | Satoh et al. .................... 600/459 |
| 7,666,138 | B2 | * | 2/2010 | Ogawa .......................... 600/442 |
| 2007/0167768 | A1 | | 7/2007 | Kristiansen |
| 2009/0024034 | A1 | | 1/2009 | Moreau-Gobard et al. |
| 2010/0262013 | A1 | | 10/2010 | Smith et al. |

FOREIGN PATENT DOCUMENTS

| | | |
|---|---|---|
| JP | 05-031107 A | 2/1993 |
| JP | 2005-137581 A | 6/2005 |

* cited by examiner

*Primary Examiner* — J M Saint Surin
(74) *Attorney, Agent, or Firm* — Wolf, Greenfield & Sacks, P.C.

(57) ABSTRACT

There is provided a signal processing apparatus including a focus position control unit that controls transmission focus positions to be focus positions of transmission waves transmitted by a plurality of ultrasonic vibrators and reception focus positions to be focus positions of reception waves received by the plurality of vibrators on the basis of position information regarding relative positions of the plurality of ultrasonic vibrators of which the relative positions are changeable.

20 Claims, 11 Drawing Sheets

FIG. 6
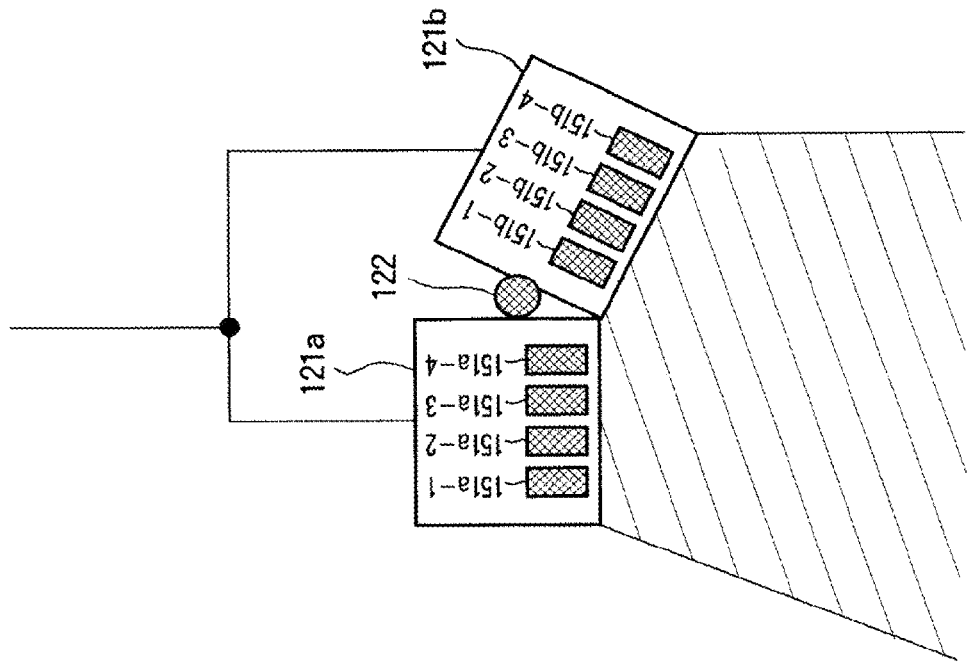
WHEN PROBES PERFORM BF COOPERATIVELY
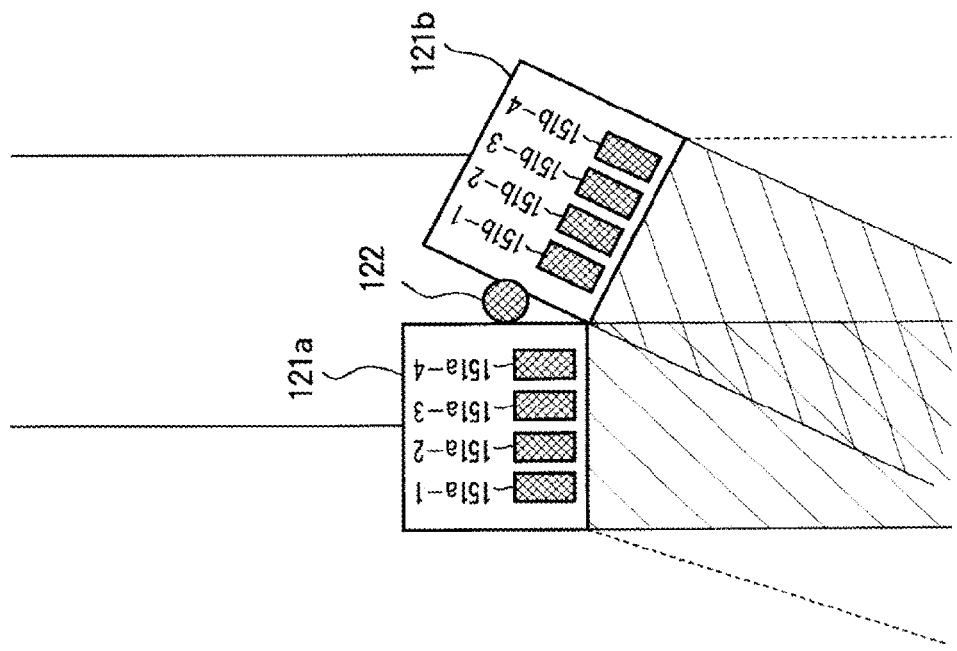
WHEN PROBES PERFORM BF INDEPENDENTLY

FIG. 7
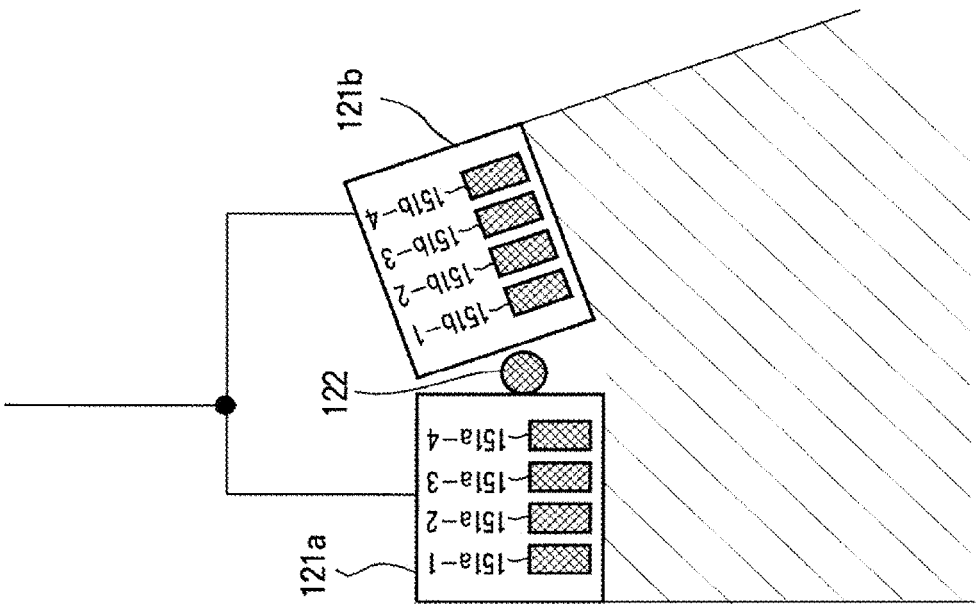
WHEN PROBES PERFORM BF COOPERATIVELY
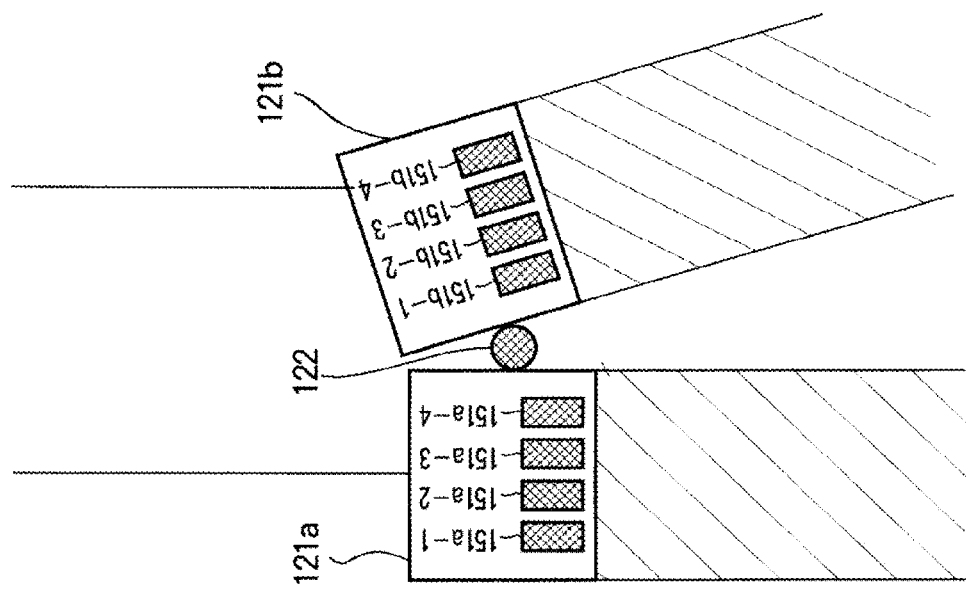
WHEN PROBES PERFORM BF INDEPENDENTLY

SIGNAL PROCESSING APPARATUS, SIGNAL PROCESSING SYSTEM, PROBE, SIGNAL PROCESSING METHOD, AND PROGRAM

CROSS REFERENCE TO RELATED APPLICATIONS

This application claims priority to Japanese Priority Patent Application JP 2011-115880, filed in the Japan Patent Office on May 24, 2011, which is herein incorporated by reference in its entirety.

BACKGROUND

The present disclosure relates to a signal processing apparatus, a signal processing system, a probe, a signal processing method, and a program, and particularly, to a signal processing apparatus, a signal processing system, a probe, a signal processing method, and a program that are suitable for imaging an ultrasonic image.

In a conventional ultrasonic diagnostic apparatus that images an ultrasonic image, beamforming for individually controlling timing (a delay amount) when each vibrator in a probe transmits or receives an ultrasonic wave to control focus positions of a transmission wave and a reception wave is performed.

In the conventional ultrasonic diagnostic apparatus, because the position of each vibrator in the probe is fixed, the delay amount to perform the beamforming is calculated previously on the basis of the position and is stored as a fixed value in a storage device of the apparatus.

Conventionally, technology for calculating a delay amount to perform beamforming on the basis of arrangement information of vibratos in a probe has been suggested (for example, refer to Japanese Laid-Open Patent Publication No. 5-31107). Conventionally, technology for connecting a plurality of probes, providing angle sensors in connection portions of the probes, calculating a relative position relation of ultrasonic images imaged using the probes on the basis of angles detected by the angle sensors, and synthesizing the ultrasonic images has been suggested (for example, refer to Japanese Laid-Open Patent Publication No. 2005-137581).

SUMMARY

However, according to the technology that is disclosed in Japanese Laid-Open Patent Publication No. 5-31107, although the appropriate delay amount is calculated according to a kind of each probe, because the position of each vibrator in the probe is fixed, an imaging range is not changed flexibly.

In addition, according to the technology that is disclosed in Japanese Laid-Open Patent Publication No. 2005-137581, because each probe individually transmits and receives the ultrasonic wave, imaging ranges may overlap or a blind area where imaging is disabled may be generated.

The present disclosure enables an ultrasonic image of a desired range to be simply and efficiently acquired.

According to a first embodiment of the present technology, there is provided a signal processing apparatus including a focus position control unit that controls transmission focus positions to be focus positions of transmission waves transmitted by a plurality of ultrasonic vibrators and reception focus positions to be focus positions of reception waves received by the plurality of vibrators on the basis of position information regarding relative positions of the plurality of ultrasonic vibrators of which the relative positions are changeable.

The plurality of vibrators may be divided and arranged into a plurality of probes, and the position information may indicate relative positions of the plurality of probes.

The focus position control unit may control the transmission focus positions of the transmission waves transmitted by the plurality of vibrators to be divided and arranged into the plurality of probes and the reception focus positions of the reception waves received by the plurality of vibrators to be divided and arranged into the plurality of probes on the basis of the relative positions of the plurality of probes.

The plurality of vibrators may be disposed in the probes in which the relative positions of the plurality of vibrators are changed by deformation, and the position information may indicate deformation degrees of the probes.

The focus position control unit may calculate a transmission delay amount indicating a transmission delay time of each vibrator and a reception delay amount indicating a reception delay time of each vibrator on the basis of the position information.

The signal processing apparatus may further include a transmission control unit that controls transmission timing of each vibrator on the basis of the transmission delay amount, and a reception control unit that synthesizes the reception signals from each vibrator while shifting time on the basis of the reception delay amount.

The signal processing apparatus may further include a signal processing unit that generates an ultrasonic image on the basis of a signal obtained by synthesizing the reception signals.

According to the first embodiment of the present technology, there is provided a signal processing method including causing a signal processing apparatus to control transmission focus positions to be focus positions of transmission waves transmitted by a plurality of ultrasonic vibrators and reception focus positions to be focus positions of reception waves received by the plurality of vibrators on the basis of position information regarding relative positions of the plurality of ultrasonic vibrators of which the relative positions are changeable.

According to the first embodiment of the present technology, a program for causing a computer may execute processing for controlling transmission focus positions to be focus positions of transmission waves transmitted by a plurality of ultrasonic vibrators and reception focus positions to be focus positions of reception waves received by the plurality of vibrators on the basis of position information regarding relative positions of the plurality of ultrasonic vibrators of which the relative positions are changeable.

According to a second embodiment of the present technology, there is provided a signal processing system including a plurality of ultrasonic vibrators of which relative positions are changeable, a sensor that detects position information regarding the relative positions of the plurality of vibrators, and a focus position control unit that controls transmission focus positions to be focus positions of transmission waves transmitted by the plurality of vibrators and reception focus positions to be focus positions of reception waves received by the plurality of vibrators on the basis of the position information.

The plurality of vibrators may be divided and arranged into a plurality of probes, and the sensor may detect relative positions of the plurality of probes.

The focus position control unit may control the transmission focus positions of the transmission waves transmitted by the plurality of vibrators to be divided and arranged into the plurality of probes and the reception focus positions of the reception waves received by the plurality of vibrators to be divided and arranged into the plurality of probes on the basis of the relative positions of the plurality of probes.

The plurality of vibrators may be disposed in the probes in which the relative positions of the plurality of vibrators are changed by deformation, and the sensor may detect deformation degrees of the probes.

The focus position control unit may calculate the transmission delay amount indicating a transmission delay time of each vibrator and the reception delay amount indicating a reception delay time of each vibrator on the basis of the position information, and may further include a transmission control unit that controls transmission timing of each vibrator on the basis of the transmission delay amount; and a reception control unit that synthesizes the reception signals from each vibrator while shifting time on a basis of the reception delay amount.

The signal processing system may further include a signal processing unit that generates an ultrasonic image on the basis of a signal obtained by synthesizing the reception signals.

The signal processing system may further include a probe unit that includes one or more probes in which the plurality of vibrators are disposed and the sensor, and a signal processing device that includes the signal processing unit. The focus position control unit, the transmission control unit, and the reception control unit may be disposed in any one of the probe unit and the signal processing device.

According to a third embodiment of the present technology, there is provided a probe unit including a plurality of probes that include ultrasonic vibrators, and a sensor that detects position information which is information used for controlling transmission focus positions to be focus positions of transmission waves transmitted by the plurality of vibrators to be divided and arranged into the plurality of probes and reception focus positions to be focus positions of reception waves received by the plurality of vibrators to be divided and arranged into the plurality of probes and indicates relative positions of the plurality of probes.

The probe unit may further include a transmission control unit that controls transmission timing of each vibrator, and a reception control unit that synthesizes a reception signal from each vibrator while shifting time.

According to a fourth embodiment of the present technology, there is provided a probe unit including a probe that includes a plurality of ultrasonic vibrators of which relative positions are changed by deformation, and a sensor that detects position information which is information used for controlling transmission focus positions to be focus positions of transmission waves transmitted by the plurality of vibrators and reception focus positions to be focus positions of reception waves received by the plurality of vibrators and indicates the relative positions of the plurality of vibrators.

The probe unit may further include a transmission control unit that controls transmission timing of each vibrator, and a reception control unit that synthesizes a reception signal from each vibrator while shifting time.

In the first embodiment of the present technology, the transmission focus positions to be focus positions of transmission waves transmitted by a plurality of ultrasonic vibrators and reception focus positions to be focus positions of reception waves received by the plurality of vibrators on the basis of position information regarding relative positions of the plurality of ultrasonic vibrators of which the relative positions are changeable are controlled.

In the second embodiment of the present technology, the position information regarding relative positions of the plurality of ultrasonic vibrators of which the relative positions are detected, and the transmission focus positions to be focus positions of transmission waves transmitted by a plurality of ultrasonic vibrators and reception focus positions to be focus positions of reception waves received by the plurality of vibrators are controlled on a basis of the position information.

In the third embodiment of the present technology, a position information which is used for controlling transmission focus positions to be focus positions of transmission waves transmitted by the plurality of ultrasonic vibrators to be divided and arranged into the plurality of probes and reception focus positions to be focus positions of reception waves received by the plurality of vibrators to be divided and arranged into the plurality of probes, and which indicates relative positions of the plurality of probes.

In the fourth embodiment of the present technology, position information which is information used for controlling transmission focus positions to be focus positions of transmission waves transmitted by the plurality of vibrators of a probe that includes a plurality of ultrasonic vibrators of which relative positions are changed by deformation and reception focus positions to be focus positions of reception waves received by the plurality of vibrators, and which indicates the relative positions of the plurality of vibrators.

According to the embodiments of the present disclosure described above, an ultrasonic image of a desired range can be acquired simply and efficiently.

BRIEF DESCRIPTION OF THE DRAWINGS

FIG. 6 is a diagram illustrating an effect of the present disclosure;

FIG. 7 is a diagram illustrating an effect of the present disclosure;

DETAILED DESCRIPTION OF THE EMBODIMENT(S)

Hereinafter, preferred embodiments of the present disclosure will be described in detail with reference to the appended drawings. The following description will be made in the order described below.
1. Embodiment
2. Modifications

1. Embodiment

[Configuration Example of Signal Processing System 101]

Figure 1:
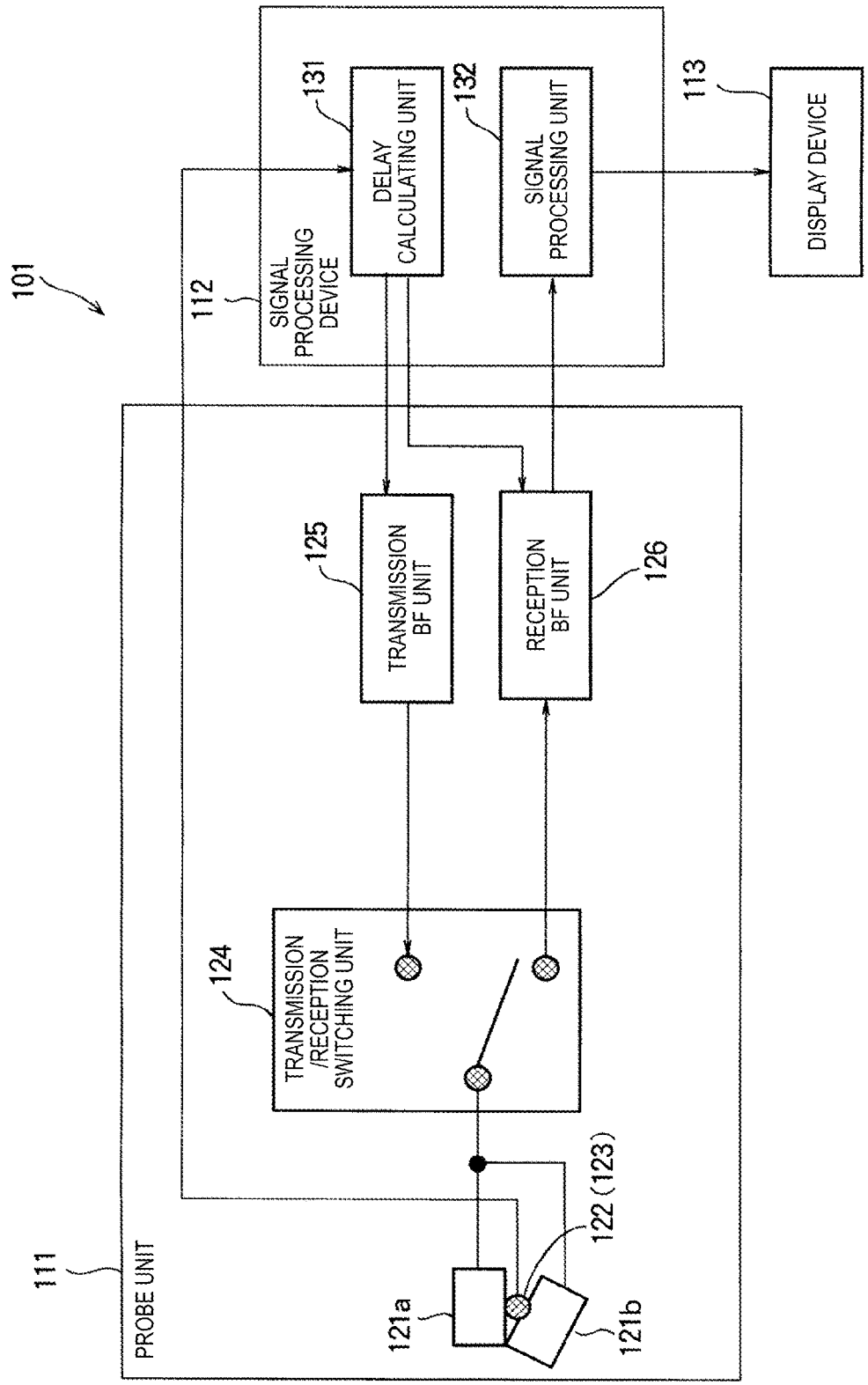
FIG. 1 is a block diagram illustrating an embodiment of a signal processing system to which the present disclosure is applied.

FIG. 1 is a block diagram illustrating an embodiment of a signal processing system to which the present disclosure is applied.

A signal processing system 101 is an apparatus that images an internal image (that is, an ultrasonic image) of an object using an ultrasonic wave and displays the image. The signal processing system 101 is used for medical purposes such as imaging an inner portion of a body of a patient or a fetus or is used for industrial purposes such as imaging a cross-section of an inner portion of a product.

The signal processing system 101 includes a probe unit 111, a signal processing device 112, and a display device 113.

The probe unit 111 transmits an ultrasonic beam (hereinafter called a transmission wave) to an object, receives a reflection wave (hereinafter called a reception wave) from the object, and detects the strength of the received reflection wave under control of the signal processing device 112.

The probe unit 111 includes a probe 121a, a probe 121b, a rotation shaft 122, an angle sensor 123, a transmission/reception switching unit 123, a transmission beamforming (BF) unit 125, and a reception beamforming (BF) unit 126.

Figure 2:
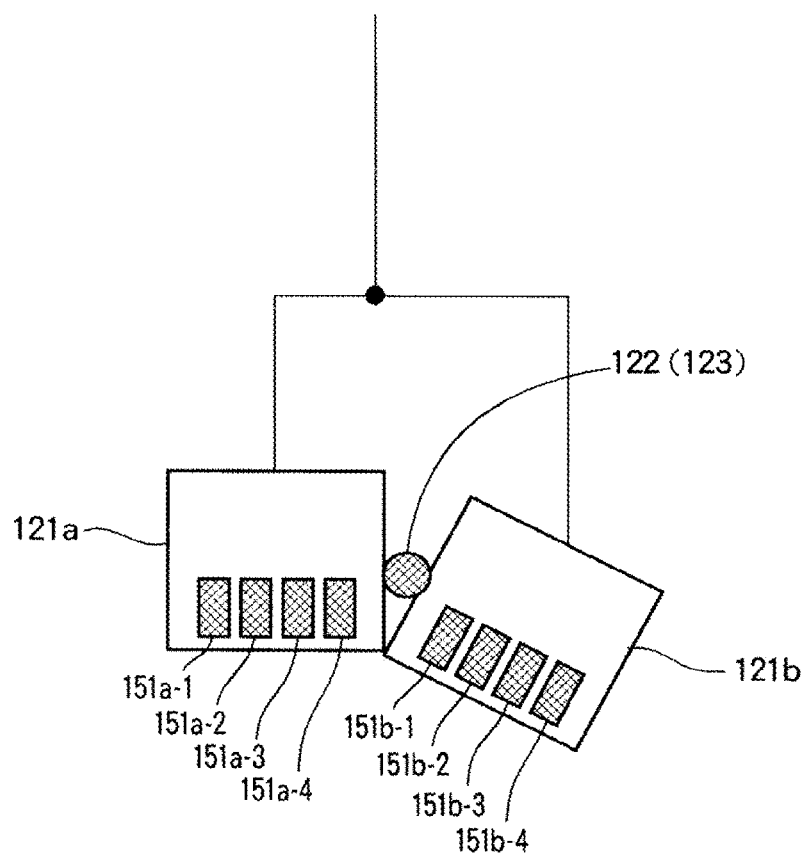
FIG. 2 is a schematic diagram illustrating a configuration example of a probe.

As illustrated in FIG. 2, the probe 121a includes vibrators 151a-1 to 151a-4. Each of the vibrators 151a-1 to 151a-4 transmits an ultrasonic wave under control of the transmission BF unit 125. Each of the vibrators 151a-1 to 151a-4 receives a reflection wave with respect to the transmitted ultrasonic wave and supplies a reception signal indicating the strength of the received reflection wave to the reception BF unit 126 through the transmission/reception switching unit 124.

As illustrated in FIG. 2, the probe 121b has the same configuration as the probe 121a and includes vibrators 151b-1 to 151b-4. Each of the vibrators 151b-1 to 151b-4 transmits an ultrasonic wave under control of the transmission BF unit 125. Each of the vibrators 151b-1 to 151b-4 receives a reflection wave with respect to the transmitted ultrasonic wave and supplies a reception signal indicating the strength of the received reflection wave to the reception BF unit 126 through the transmission/reception switching unit 124.

The probes 121a and 121b are connected by a hinge structure including the rotation shaft 122 and a relative angle between the probes 121a and 121b can be changed using the rotation shaft 122 as a supporting point. As a result, relative positions between the vibrators 151a-1 to 151a-4 of the probe 121a and the vibrators 151b-1 to 151b-4 of the probe 121b change.

The angle sensor 123 is embedded in the rotation shaft 122. The angle sensor 123 detects a rotation angle of the rotation shaft 122 and supplies a sensor signal indicating the detected rotation angle to a delay calculating unit 131 of the signal processing device 112.

Hereinafter, when the probes 121a and 121b do not need to be individually distinguished, the probes 121a and 121b are simply called the probes 121. When the vibrators 151a-1 to 151a-4 do not need to be individually distinguished, the vibrators 151a-1 to 151a-4 are simply called the vibrators 151a and when the vibrators 151b-1 to 151b-4 do not need to be individually distinguished, the vibrators 151b-1 to 151b-4 are simply called the vibrators 151b. When the vibrators 151a-1 to 151b-4 do not need to be individually distinguished, the vibrators 151a-1 to 151b-4 are simply called the vibrators 151.

The transmission/reception switching unit 124 switches an embedded switch, selects any one of the transmission BF unit 125 and the reception BF unit 126, and is connected to the probe 121.

The transmission BF unit 125 performs the transmission beamforming, under the control of the signal processing device 112. That is, the transmission BF unit 125 controls transmission timing of the ultrasonic wave from each vibrator 151 of the probe 121 and controls a waveform of an ultrasonic beam to be formed by the ultrasonic wave transmitted from each vibrator 151.

The reception BF unit 126 performs the reception beamforming under the control of the signal processing device 112. That is, the reception BF unit 126 synthesizes a reception signal supplied from each vibrator 151 of each probe 121 while shifting time and generates a signal indicating the strength of a reflection wave from each position of the object (hereinafter called a reflection wave detection signal). The reception BF unit 126 supplies the generated reflection wave detection signal to the signal processing unit 132 of the signal processing device 112.

The signal processing device 112 controls the probe unit 111 and generates an ultrasonic image showing an inner portion of the object on the basis of the reflection wave detection signal supplied from the probe unit 111.

The signal processing device 112 includes the delay calculating unit 131 and the signal processing unit 132.

The delay calculating unit 131 calculates a delay amount (hereinafter called a transmission delay amount) indicating a transmission delay time of each vibrator 151 of the probe 121 on the basis of the detection result of the rotation angle of the rotation shaft 122 by the angle sensor 123. The delay calculating unit 131 supplies the transmission delay amount to the transmission BF unit 125 and controls the transmission beamforming by the transmission BF unit 125.

The delay calculating unit 131 calculates a delay amount (hereinafter called a reception delay amount) indicating a reception delay time of each vibrator 151 of the probe 121 on the basis of the detection result of the rotation angle of the rotation shaft 122 by the angle sensor 123. The delay calculating unit 131 supplies the reception delay amount to the reception BF unit 126 and controls the reception beamforming by the reception BF unit 126.

The signal processing unit 132 generates the ultrasonic image showing the inner portion of the object on the basis of the reflection wave detection signal supplied from the reception BF unit 126. The signal processing unit 132 supplies the generated ultrasonic image to the display device 113.

The display device 113 displays the ultrasonic image that is generated by the signal processing unit 132.

[Processing of Signal Processing System 101]

Figure 3:
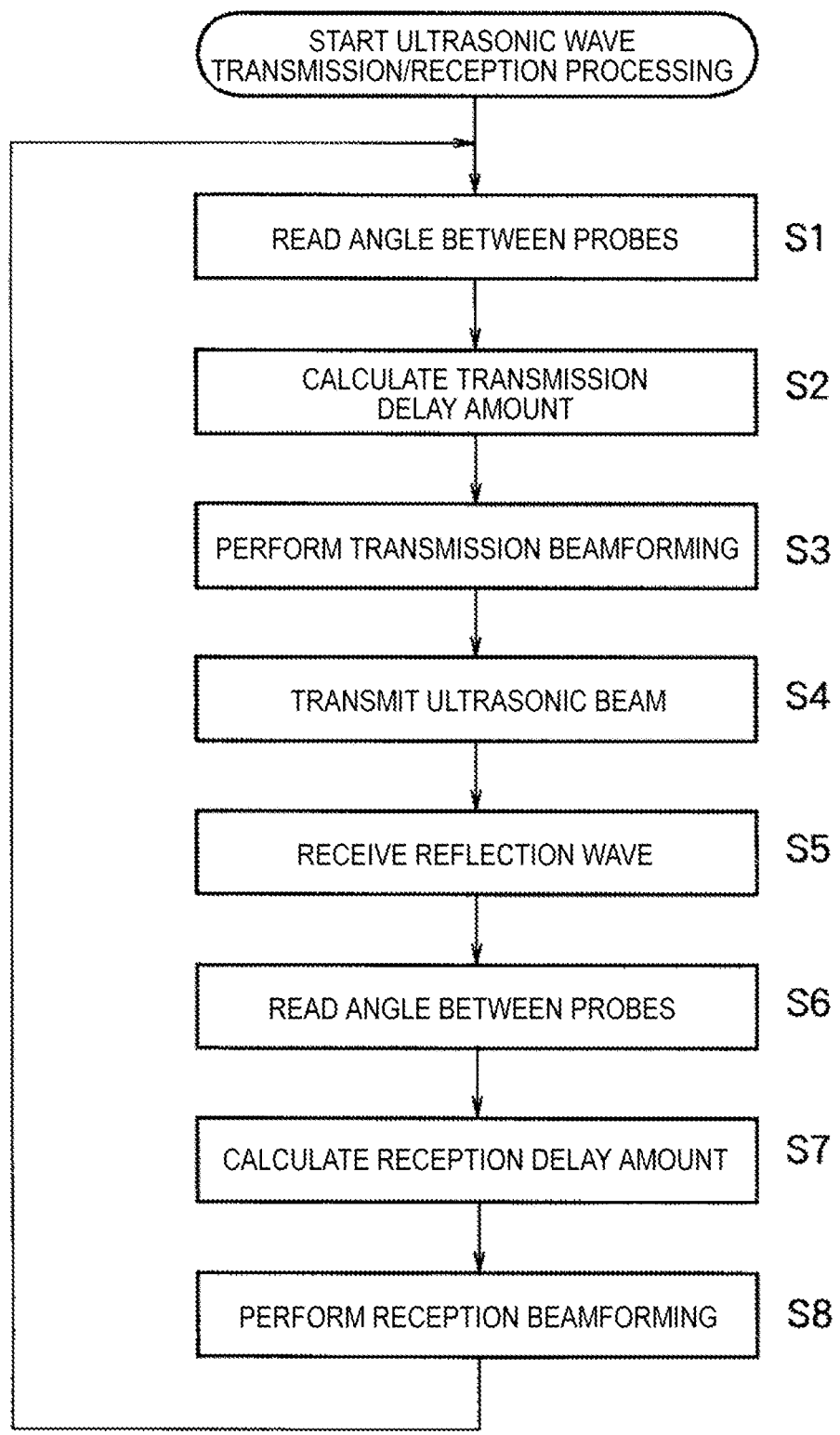
FIG. 3 is a flowchart illustrating ultrasonic wave transmission/reception processing that is executed by a signal processing system.
Figure 4:
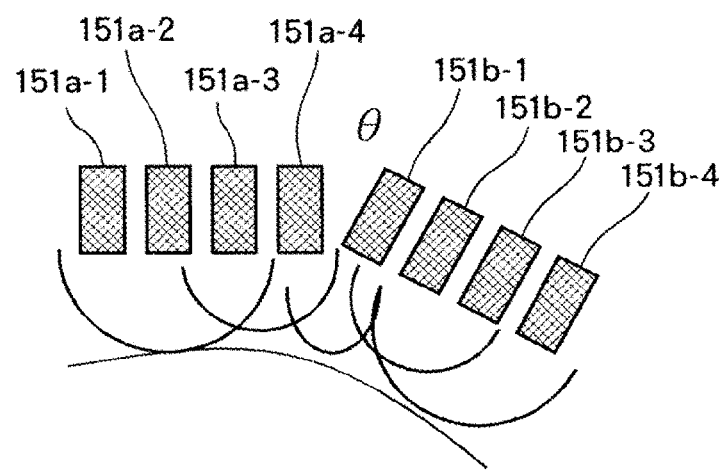
FIG. 4 is a diagram illustrating an example of a method of setting valid vibrators.
Figure 5:
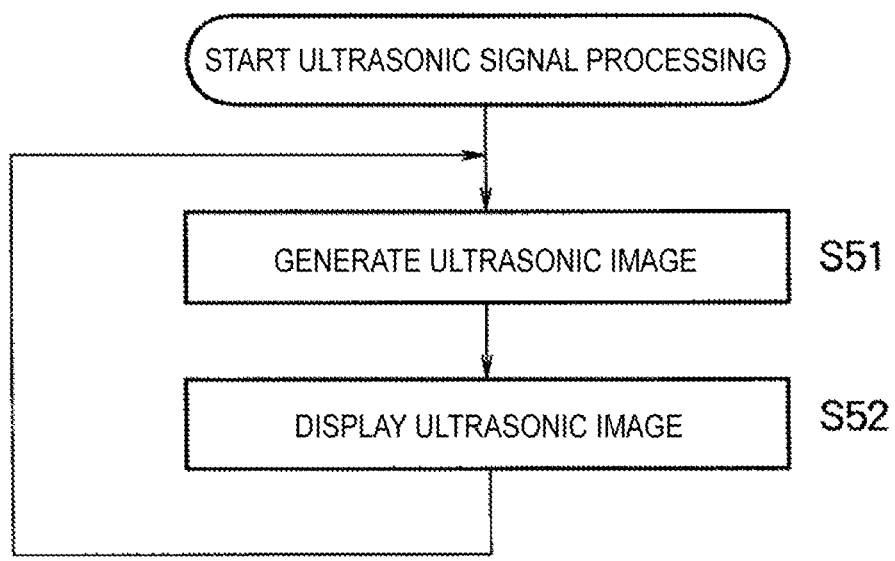
FIG. 5 is a flowchart illustrating ultrasonic signal processing that is executed by the signal processing system.

Next, processing of the signal processing system 101 will be described with reference to FIGS. 3 to 5.

[Ultrasonic Wave Reception Processing]

First, ultrasonic wave reception processing that is executed by the probe unit 111 and the delay calculating unit 131 of the signal processing device 112 of the signal processing system 101 will be described with reference to a flowchart of FIG. 3.

The processing starts when an instruction of a processing start is input through an input unit (not illustrated in the drawings) and ends when an instruction of a processing end is input.

In step S1, the delay calculating unit 131 reads an angle between the probes 121 on the basis of a sensor signal supplied from the angle sensor 123.

In step S2, the delay calculating unit 131 calculates the transmission delay amount.

In this case, the probe unit 111 scans an ultrasonic beam (transmission wave) transmitted by each vibrator 151 of the probe 121 in a predetermined scanning direction (for example, in a radial fashion or in a direction vertical to a traveling direction of the ultrasonic beam).

The probe unit 111 performs electronic focusing of the ultrasonic beam. That is, the probe unit 111 switches the vibrator 151 (hereinafter called a valid vibrator) used in transmission/reception of the ultrasonic beam, controls transmission timing of each valid vibrator, and controls a phase of the ultrasonic wave transmitted from each valid vibrator. Thereby, a focus position (hereinafter called a transmission focus position) of the ultrasonic beam that is formed by the ultrasonic wave transmitted from the valid vibrator is controlled.

With respect to one scanning line, one transmission focus position may be set and the ultrasonic beam may be transmitted only once or multi-step focusing in which the ultrasonic beam is transmitted many times by setting a plurality of transmission focus positions having different depths may be performed. However, if the plurality of transmission focus positions are set, a high-definition ultrasonic image can be obtained. Meanwhile, when the number of times of transmitting/receiving the ultrasonic beam increases, a frame rate becomes low. Therefore, the number of times of setting the transmission focus position is set on the basis of the required image quality or frame rate.

A shape of a scanning surface that is a range where the ultrasonic beam is scanned may be set by a user or may be automatically set on the basis of the angle between the probes 121.

Therefore, the delay calculating unit 131 sets a plurality of transmission focus positions used when an ultrasonic image of one frame is imaged on the basis of the number of scanning lines and the number of transmission focus positions for each scanning line. The delay calculating unit 131 selects a transmission focus position of a subsequently transmitted ultrasonic beam from the plurality of transmission focus positions.

The delay calculating unit 131 selects a plurality of valid vibrators used in transmission/reception of a subsequent ultrasonic beam, according to the selected transmission focus position. At this time, the valid vibrators may be provided over the two probes 121.

The number of valid vibrators may be fixed or varied. In the case of the former, for example, the number of valid vibrators is fixed to a predetermined value (for example, 4) and the positions of the valid vibrators are shifted according to the transmission focus positions.

Meanwhile, in the case of the latter, for example, the positions of the valid vibrators and the number of valid vibrators are changed according to the transmission focus positions. For example, as illustrated in FIG. 4, after a set of vibrators 151a-1 to 151a-3 is set as the valid vibrators, the number of valid vibrators or the positions thereof can be changed in order of a set of vibrators 151a-2 to 151a-4, a set of vibrators 151a-4 and 151b-1, a set of vibrators 151b-1 to 151b-3, and a set of vibrators 151b-2 to 151b-4. In FIG. 4, θ shows an angle between the probes 121a and 121b.

Alternatively, all of the vibrators 151 of the probes 121a and 121b may be set as the valid vibrators at all times.

The vibrators 151 used for transmission and the vibrators 151 used for reception are not necessarily matched with each other. For example, the reception wave of the ultrasonic beam may be received by a combination of the vibrators 151 different from a combination of the vibrators 151 used for the transmission.

Hereinafter, it is assumed that the ultrasonic wave is transmitted and received using the same vibrator 151, unless otherwise specified.

The delay calculating unit 131 calculates the relative positions between the valid vibrators on the basis of the angle between the probes 121 and known geometrical information. In this case, the geometrical information includes distances between the vibrators 151 in each probe 121 and distances from the rotation shaft 122 to the vibrators 151.

The delay calculating unit 131 calculates the distances between the vibrators and the transmission focus positions and the difference of the distances on the basis of the relative positions between the valid vibrators.

The delay calculating unit 131 calculates a transmission delay amount indicating delayed time of timing when the ultrasonic wave is transmitted from each valid vibrator on the basis of the difference of times when the ultrasonic wave transmitted from each valid vibrator reaches the transmission focus position. That is, the delay calculating unit 131 calculates the transmission delay amount with respect to each valid vibrator, such that the focus position formed by the ultrasonic wave transmitted from each valid vibrator is matched with the set transmission focus position.

When the transmission delay amount is calculated, in addition to the parameter described above, other parameters such as a display mode and gain setting may be used.

The delay calculating unit 131 transmits information indicating the transmission delay amount with respect to each valid vibrator to the transmission BF unit 125.

In step S3, the transmission BF unit 125 performs the transmission beamforming. Specifically, the transmission BF unit 125 calculates a waveform of the ultrasonic wave transmitted from each valid vibrator on the basis of the transmission delay amount of each valid vibrator calculated by the delay calculating unit 131.

In step S4, the probe unit 111 transmits the ultrasonic beam. Specifically, the transmission/reception switching unit 124 switches the switch to the side of the transmission BF unit 125. The transmission BF unit 125 supplies a control signal to each valid vibrator through the transmission/reception switching unit 124 and transmits the ultrasonic wave of the waveform calculated in step S3.

The ultrasonic beam that is formed by the ultrasonic wave transmitted from each valid vibrator forms a focus at the transmission focus position set in step S2.

In step S5, the probe unit 111 receives the reflection wave. Specifically, the transmission/reception switching unit 124 switches the switch to the side of the reception BF unit 126. Each valid vibrator receives the reflection wave with respect to the ultrasonic beam transmitted in step S4. Each valid vibrator converts the strength of the received reflection wave into an electric signal and supplies a reception signal indicating a time-series change of the strength of the received reflection wave to the reception BF unit 126 through the transmission/reception switching unit 124. The reception BF unit 126 amplifies the reception signal from each valid vibrator and performs A/D conversion to convert the signal into a digital signal.

In step S6, the delay calculating unit 131 reads the angle between the probes 121, similar to the process of step S1.

In step S7, the delay calculating unit 131 calculates the reception delay amount.

In this case, the probe unit 111 performs dynamic focusing for receiving the reflection wave (reception wave) received by the valid vibrator while changing the focus position (hereinafter called a reception focus position) by digital processing, with respect to one-time transmission of the ultrasonic beam.

Therefore, the delay calculating unit 131 sets a plurality of reception focus positions to scanning lines of the ultrasonic beams transmitted in step S4.

The number of times of setting the reception focus position is set on the basis of the required image quality or frame rate. The number of reception focus positions is generally set to be larger than the number of transmission focus positions.

The delay calculating unit 131 calculates the relative positions between the valid vibrators on the basis of the angle between the probes 121 and the known geometrical information. The delay calculating unit 131 calculates the distances between the vibrators and the reception focus positions and the difference of the distances with respect to all of the set reception focus positions on the basis of the relative positions between the valid vibrators.

In this case, the reflection wave from the certain reception focus position reaches the valid vibrators with the time difference according to the distance from the reception focus position. Therefore, if the reception signals supplied from the valid vibrators are synthesized with the time difference, a reflection wave detection signal that indicates the strength of the reflection wave from the reception focus position can be generated.

The delay calculating unit 131 calculates a reception delay amount indicating a shift amount of a time direction of each reception signal when the reception signals generated by the valid vibrators are generated on the basis of the difference of times when the reflection wave from each reception focus position reaches each valid vibrator.

In step S8, the reception BF unit 126 performs the reception beamforming. Specifically, the reception BF unit 126 selects one reception focus position and synthesizes the reception signals from the valid vibrators while shifting time on the basis of the reception delay amount with respect to the selected reception focus position. Thereby, a reflection wave detection signal that indicates the strength of the reflection wave from the selected reception focus position is generated.

The reception BF unit 126 executes the same processing with respect to all of the reception focus positions. Thereby, a reflection wave detection signal with respect to each reception focus position that is set to the current scanning line is generated.

The reception BF unit 126 transmits a reflection wave detection signal at each reception focus position to the signal processing unit 132.

Then, the process returns to step S1 and the processes of steps S1 to S8 are repetitively executed.

As such, the ultrasonic beam is scanned while the transmission focus position is changed and the reflection wave detection signal that indicates the strength of the reflection wave from the reception focus position to each scanning line is generated on the basis of the reflection wave and is supplied to the signal processing unit 132.

[Ultrasonic Signal Processing]

Next, ultrasonic signal processing corresponding to the ultrasonic transmission/reception processing of FIG. 3 that is executed by the signal processing unit 132 of the signal processing device 112 and the display device 113 will be described with reference to a flowchart of FIG. 5.

In step S51, the signal processing unit 132 generates an ultrasonic image. Specifically, the signal processing unit 132 calculates the strength of the reflection wave from each reception focus position on the basis of each reflection wave detection signal when the reflection wave detection signals corresponding to one frame are accumulated. The signal processing unit 132 generates an ultrasonic image showing an inner portion of the object on the basis of the strength of the reflection wave at each reception focus position. The signal processing unit 132 supplies the generated ultrasonic image to the display device 113.

In step S52, the display device 113 displays the ultrasonic image that is generated by the signal processing unit 132.

Then, the process returns to step S51 and the processes of steps S51 and S52 are repetitively executed.

In this way, the relative positions between the probes 121 are detected in real time and the transmission delay amount and the reception delay amount are sequentially calculated on the basis of the relative positions between the vibrators 151 calculated indirectly by the relative positions between the probes 121. Using the transmission delay amount and the reception delay amount, the transmission beamforming and the reception beamforming are appropriately performed according to the relative positions between the probes 121 (vibrators 151).

The beamforming can be performed in a state in which the vibrators 151 to be divided into the different probes 121 and to be arranged cooperate with each other.

An effect when the probes 121 perform the beamforming cooperatively as in the signal processing system 101 will be described with reference to FIGS. 6 to 8, while comparing the effect with an effect when the probes 121 perform the beamforming independently as in the related art.

Figure 8:
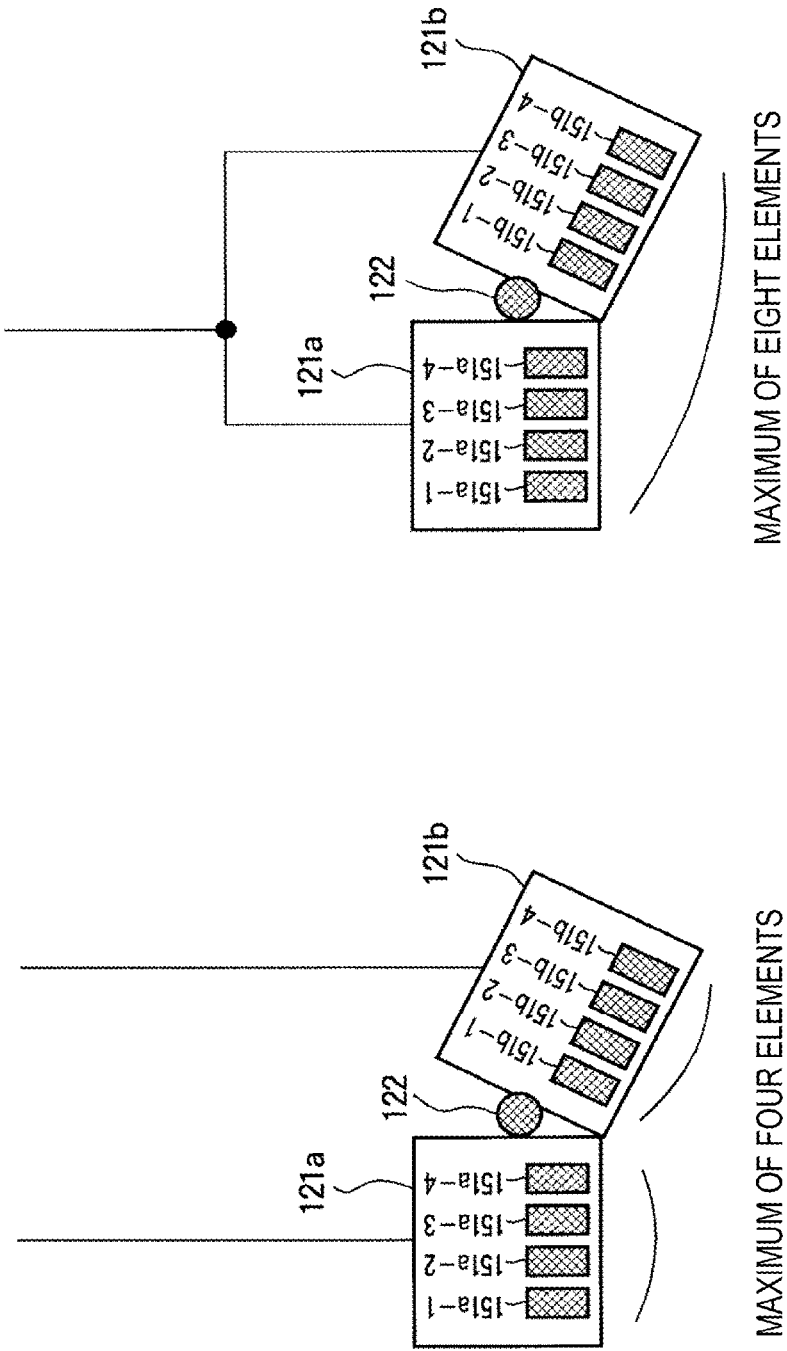
FIG. 8 is a diagram illustrating an effect of the present disclosure.

A left portion of each of FIGS. 6 to 8 illustrates an example of the case in which the probes 121 perform the beamforming independently and a right portion thereof illustrates an example of the case in which the probes 121 perform the beamforming cooperatively. Portions indicated with diagonal lines in each of FIGS. 6 to 8 illustrate scanning ranges of the ultrasonic beams.

For example, when the probes 121 perform the beamforming independently, as illustrated by the left portion of FIG. 6, the probes 121 are oriented toward the inner side and an overlapping area of the scanning ranges of the ultrasonic beams may be generated. In the overlapping area of the scanning ranges, the ultrasonic beams are scanned wastefully. As a result, delay of processing time is generated.

For example, when the probes 121 perform the beamforming independently, as illustrated by the left portion of FIG. 7, the probes 121 are oriented toward the outer side and an area that becomes a blind area due to non-scanning of the ultrasonic beams may be generated.

Meanwhile, when the probes 121 perform the beamforming cooperatively, as illustrated by the right portions of FIGS. 6 and 7, the ultrasonic beams can be efficiently scanned in a desired range without generating the overlapping scanning range or the blind area, regardless of a direction of each probe 121. The user can scan the ultrasonic wave simply in the desired range by only adjusting the angle between the probes 121. Thereby, an ultrasonic image of the desired range can be simply and efficiently acquired.

When the probes 121 perform the beamforming independently, as illustrated by the left side of FIG. 8, a maximum of four vibrators 151 can be operated cooperatively. Meanwhile, when the probes 121 perform the beamforming cooperatively, as illustrated by the right side of FIG. 8, a maximum of eight vibrators 151 can be operated cooperatively.

As a result, an obtained information amount can be increased and a high-definition ultrasonic image that is resistant to noise can be obtained. A degree of freedom of the setting positions of the transmission focus positions or the reception focus positions becomes high and an effect of the multi-step focusing can be obtained more precisely.

When the plurality of probes are used, if the transmission and reception timings of the plurality of probes are not appropriately controlled, the transmission wave and the reception wave are mixed with each other and reliability of data is lowered.

Therefore, when the probes 121 are controlled independently as in the related art, the safest sequential processing needs to be executed to prevent interference between the transmission wave and the reception wave. That is, after the ultrasonic beams are scanned by one probe 121, the ultrasonic beams need to be scanned by the next probe 121.

Meanwhile, when the probes 121 are controlled cooperatively, scheduling of the transmission and the reception can be performed efficiently to avoid the interference between the ultrasonic beams. An interference simulation can be performed on the basis of the geometrical information and an interference component can be removed from the reception signal.

2. Modifications

Hereinafter, modifications of the embodiment of the present disclosure will be described.

[First Modification]

The mechanism that changes the relative positions between the probes 121 is not limited to the example described above and other mechanisms may be adopted.

The mechanisms for detecting the relative positions between the probes 121 and the number thereof are not limited to the example described above. That is, a mechanism that detects the relative positions between the probes 121 and detects other parameters to detect the relative positions between the vibrators 151 indirectly, for example, a distance, a direction, bending, a distortion, a torsion, a translational motion, and a rotary motion, may be adopted.

[Second Modification]

The number of probes is not limited to the example described above and the present disclosure can be applied to the case in which three or more probes are used cooperatively.

The number of vibrators in each probe is not limited to the example described above and may be set to one or more. The number of vibrators in each probe is not necessarily matched.

[Third Modification]

The example of the case in which the relative positions between the probes change and the relative positions of the vibrators in the probe are fixed is described above. However, the present disclosure can be applied to the case in which the relative positions of the vibrators in the probe change.

Figure 9:
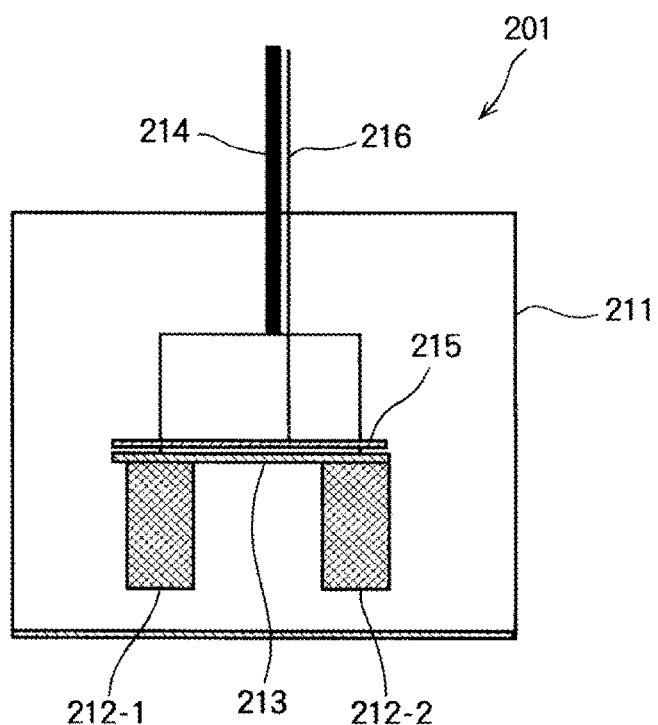
FIG. 9 is a cross-sectional view schematically illustrating a modification of the probe.
Figure 10:
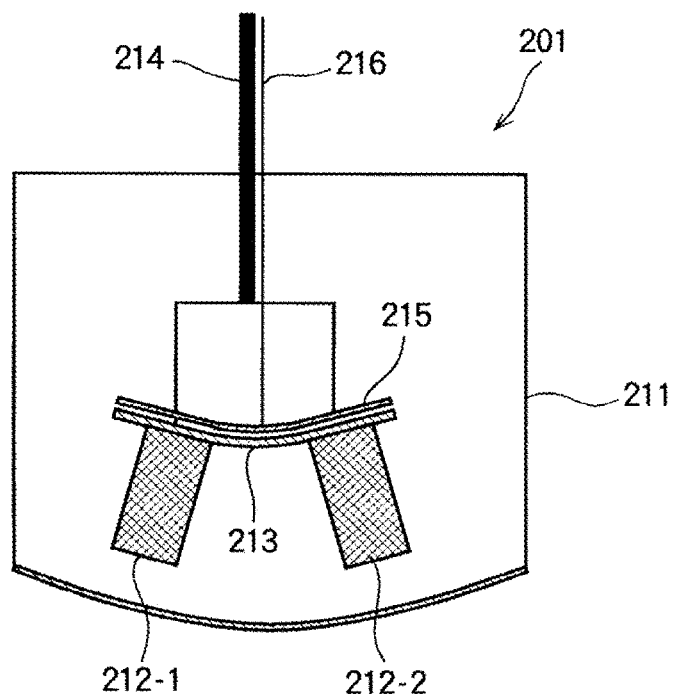
FIG. 10 is a cross-sectional view schematically illustrating a modification of the probe.

FIGS. 9 and 10 are cross-sectional views schematically illustrating an example of the case in which the relative positions of the vibrators in the probe change.

In a probe 201, vibrators 212-1 and 212-2 are provided in a casing 211 made of a flexible material or an elastic material. The vibrators 212-1 and 212-2 are attached to a flat member 213 made of a flexible material. The vibrators 212-1 and 212-2 are connected to another device or component (for example, the transmission/reception switching unit 124 of FIG. 1) through a control line 214.

A member 213 is provided with a bending sensor 215 to detect a bending degree of the member 213. The bending sensor 215 is connected to another device or component (for example, the delay calculating unit 131 of FIG. 1) through a control line 216.

In the probe 201, the casing 211 has flexibility or elasticity and the member 213 has flexibility. Therefore, as illustrated in FIG. 10, the relative positions between the vibrators 212-1 and 212-2 can be changed in the probe 201 by bending or twisting the casing 211 to deform the casing 211.

The change of the relative positions between the vibrators 212-1 and 212-2 is detected on the basis of a detection value of the bending sensor 215 and the geometrical information. As described above, the transmission delay amount and the reception delay amount can be calculated on the relative positions between the vibrators 212-1 and 212-2 and the transmission beamforming and the reception beamforming can be performed.

In this example, the case in which the probe includes the two vibrators has been described to simplify the description. The probe may include three or more vibrators and the relative positions between the vibrators may be detected.

The mechanism for changing the relative positions of the vibrators in the probe is not limited to the example described above. For example, the same hinge mechanism as the probe unit 111 of FIG. 1 may be provided in one probe and the relative positions between the vibrators in the probe may be changed by the hinge mechanism.

The mechanisms for detecting the relative positions of the vibrators in the probe and the number thereof are not limited to the example described above. For example, a deformation angle of the member 213 may be detected by a mechanism other than the bending sensor 215.

Similar to the probe unit 111 of FIG. 1, the plurality of probes 201 may be connected and the relative positions between the probes may be detected. The transmission beamforming and the reception beamforming may be performed on the basis of the relative positions of the vibrators in the probes and the relative positions of the vibrators between the probes.

The probe such as the probe 121 in which the positions of the vibrators are fixed and the probe such as the probe 201 in which the positions of the vibrators are fixed may be combined and the combined probes may be used.

[Fifth Modification]

In the above description, the angle between the probes 121 may be read and the transmission delay amount and the reception delay amount may be updated whenever the transmission of the ultrasonic beam and the reception of the reflection wave are performed. However, the update frequency may be decreased. For example, the transmission delay amount and the reception delay amount may be updated for every frame or several frames.

The update frequency of the reception delay amount is preferably set to be higher than the update frequency of the transmission delay amount.

[Sixth Modification]

The configuration of the signal processing system 101 is not limited to the example illustrated in FIG. 1 and the signal processing system 101 may have another configuration.

For example, two devices among the probe unit 111, the signal processing device 112, and the display device 113 or all of them may be configured by one device.

In addition, a part of the structural elements of the probe units 111 may be disposed in the signal processing device 112 and a part of the structural elements of the signal processing device 112 may be disposed in the probe unit 111. For example, the delay calculating unit 131 may be disposed on the probe unit 111 and the transmission BF unit 125 and the reception BF unit 126 may be provided in the signal processing device 112.

[Seventh Modification]

The transmission beamforming method and the reception beamforming method are not limited to the example described above and arbitrary methods may be used.

In the above description, the beamforming is performed by the digital processing. However, the present disclosure can be applied to the case in which the beamforming is performed by analog processing.

[Eighth Modification]

The present disclosure is not limited to the case in which the ultrasonic beams are scanned two-dimensionally and can be applied to the case in which the ultrasonic beams are scanned three-dimensionally. A method of scanning the ultrasonic beams three-dimensionally is not limited to a specific method. For example, the vibrators may be disposed three-dimensionally and the probes that are disposed two-dimensionally may be mechanically moved.

[Configuration Example of Computer]

The series of processes described above can be realized by hardware or software. When the series of processes is executed by the software, a program forming the software is installed in a computer. In this case, examples of the computer include a computer embedded in dedicated hardware and a general-purpose computer in which various programs can be installed and various functions can be executed.

Figure 11:
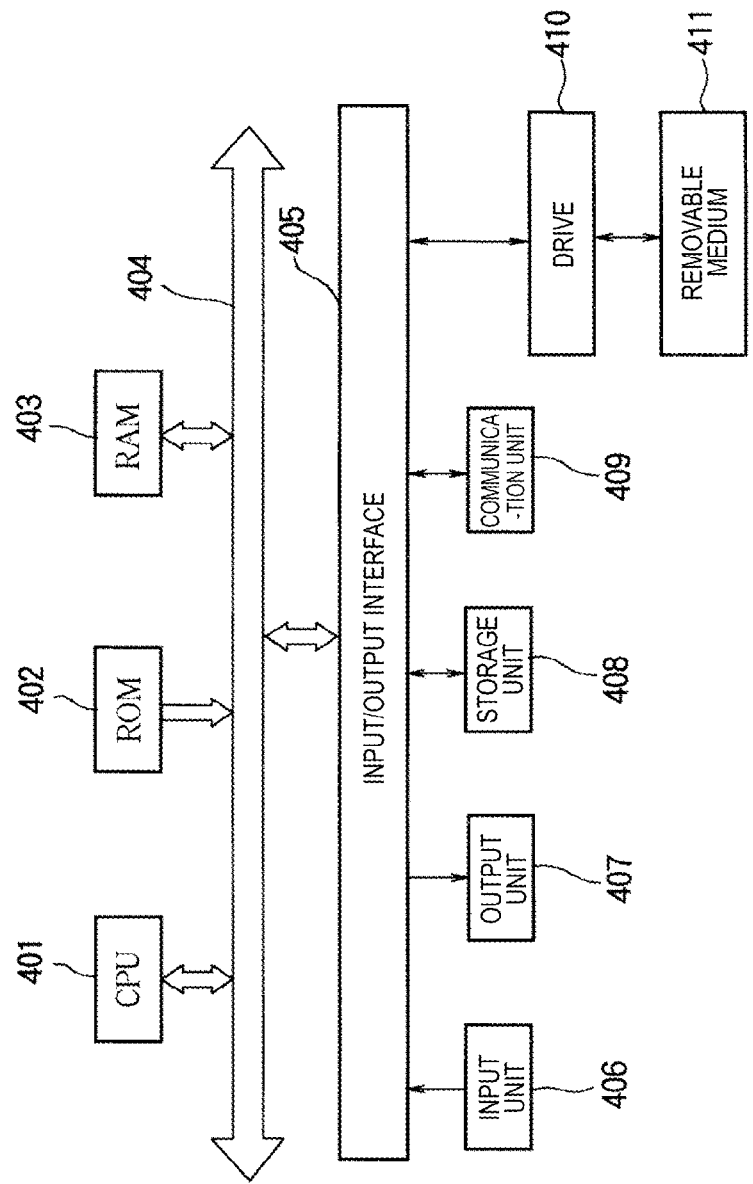
FIG. 11 is a block diagram illustrating a configuration example of a computer.

FIG. 11 is a block diagram illustrating a configuration example of hardware of a computer that executes the series of processes by a program.

In a computer, a central processing unit (CPU) 401, a read only memory (ROM) 402, and a random access memory (RAM) 403 are connected mutually by a bus 404.

An input/output interface 405 is connected to the bus 404. An input unit 406, an output unit 407, a storage unit 408, a communication unit 409, and a drive 410 are connected to the input/output interface 405.

The input unit 406 includes a keyboard, a mouse, and a microphone. The output unit 407 includes a display and a speaker. The storage unit 408 is configured using a hard disk or a non-volatile memory. The communication unit 409 is configured using a network interface. The drive 410 drives removable media 411 such as a magnetic disk, an optical disc, a magneto optical disc, or a semiconductor memory.

In the computer that is configured as described above, the CPU 401 loads the programs stored in the storage unit 408 to the RAM 403 through the input/output interface 405 and the bus 404 and executes the programs, and the series of processes is executed.

The programs that are executed by the computer (CPU 401) may be recorded in the removable media 411 functioning as package media and may be provided. The programs may be provided through wired or wireless transmission media such as a local area network, the Internet, and digital satellite broadcasting.

In the computer, by mounting the removable media 411 to the drive 410, the programs may be installed in the storage unit 408 through the input/output interface 405. The programs may be received by the communication unit 409 through the wired or wireless transmission media and may be installed in the storage unit 408. The programs may be installed previously in the ROM 402 or the storage unit 408.

The programs that are executed by the computer may be programs that are processed in time series according to the order described in the present disclosure and may be programs that are processed in parallel or at necessary timing when calling is performed.

In the present disclosure, the term "system" means a general apparatus that is configured using a plurality of devices and mechanisms.

It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1)

A signal processing apparatus including:

a focus position control unit that controls transmission focus positions to be focus positions of transmission waves transmitted by a plurality of ultrasonic vibrators and reception focus positions to be focus positions of reception waves received by the plurality of vibrators on the basis of position information regarding relative positions of the plurality of ultrasonic vibrators of which the relative positions are changeable.

(2)

The signal processing apparatus according to (1), wherein the plurality of vibrators are divided and arranged into a plurality of probes, and the position information indicates relative positions of the plurality of probes.

(3)

The signal processing apparatus according to (2), wherein the focus position control unit controls the transmission focus positions of the transmission waves transmitted by the plurality of vibrators to be divided and arranged into the plurality of probes and the reception focus positions of the reception waves received by the plurality of vibrators to be divided and arranged into the plurality of probes on the basis of the relative positions of the plurality of probes.

(4)

The signal processing apparatus according to (1), wherein the plurality of vibrators are disposed in the probes in which the relative positions of the plurality of vibrators are changed by deformation, and the position information indicates deformation degrees of the probes.

(5)

The signal processing apparatus according to any one of (1) to (4), wherein the focus position control unit calculates a transmission delay amount indicating a transmission delay time of each vibrator and a reception delay amount indicating a reception delay time of each vibrator on the basis of the position information.

(6)

The signal processing apparatus according to (5), further including:

a transmission control unit that controls transmission timing of each vibrator on the basis of the transmission delay amount; and a reception control unit that synthesizes the reception signals from each vibrator while shifting time on the basis of the reception delay amount.

(7)

The signal processing apparatus according to (6), further including:

a signal processing unit that generates an ultrasonic image on the basis of a signal obtained by synthesizing the reception signals.

(8)
A signal processing method including:
causing a signal processing apparatus to control transmission focus positions to be focus positions of transmission waves transmitted by a plurality of ultrasonic vibrators and reception focus positions to be focus positions of reception waves received by the plurality of vibrators on the basis of position information regarding relative positions of the plurality of ultrasonic vibrators of which the relative positions are changeable.

(9)
A program for causing a computer to execute:
processing for controlling transmission focus positions to be focus positions of transmission waves transmitted by a plurality of ultrasonic vibrators and reception focus positions to be focus positions of reception waves received by the plurality of vibrators on the basis of position information regarding relative positions of the plurality of ultrasonic vibrators of which the relative positions are changeable.

(10)
A signal processing system including:
a plurality of ultrasonic vibrators of which relative positions are changeable;
a sensor that detects position information regarding the relative positions of the plurality of vibrators; and
a focus position control unit that controls transmission focus positions to be focus positions of transmission waves transmitted by the plurality of vibrators and reception focus positions to be focus positions of reception waves received by the plurality of vibrators on the basis of the position information.

(11)
The signal processing system according to (10),
wherein the plurality of vibrators are divided and arranged into a plurality of probes, and
the sensor detects relative positions of the plurality of probes.

(12)
The signal processing system according to (11),
wherein the focus position control unit controls the transmission focus positions of the transmission waves transmitted by the plurality of vibrators to be divided and arranged into the plurality of probes and the reception focus positions of the reception waves received by the plurality of vibrators to be divided and arranged into the plurality of probes on the basis of the relative positions of the plurality of probes.

(13)
The signal processing system according to (10),
wherein the plurality of vibrators are disposed in the probes in which the relative positions of the plurality of vibrators are changed by deformation, and
the sensor detects deformation degrees of the probes.

(14)
The signal processing system according to (10),
wherein the focus position control unit calculates the transmission delay amount indicating a transmission delay time of each vibrator and the reception delay amount indicating a reception delay time of each vibrator on the basis of the position information, and further includes:
a transmission control unit that controls transmission timing of each vibrator on the basis of the transmission delay amount; and
a reception control unit that synthesizes the reception signals from each vibrator while shifting time on a basis of the reception delay amount.

(15)
The signal processing system according to (14), further including:
a signal processing unit that generates an ultrasonic image on the basis of a signal obtained by synthesizing the reception signals.

(16)
The signal processing system according to (15), further including:
a probe unit that includes one or more probes in which the plurality of vibrators are disposed and the sensor; and
a signal processing device that includes the signal processing unit,
wherein the focus position control unit, the transmission control unit, and the reception control unit are disposed in any one of the probe unit and the signal processing device.

(17)
A probe unit including:
a plurality of probes that include ultrasonic vibrators; and
a sensor that detects position information which is information used for controlling transmission focus positions to be focus positions of transmission waves transmitted by the plurality of vibrators to be divided and arranged into the plurality of probes and reception focus positions to be focus positions of reception waves received by the plurality of vibrators to be divided and arranged into the plurality of probes and indicates relative positions of the plurality of probes.

(18)
The probe unit according to (17), further including:
a transmission control unit that controls transmission timing of each vibrator; and
a reception control unit that synthesizes a reception signal from each vibrator while shifting time.

(19)
A probe unit including:
a probe that includes a plurality of ultrasonic vibrators of which relative positions are changed by deformation; and
a sensor that detects position information which is information used for controlling transmission focus positions to be focus positions of transmission waves transmitted by the plurality of vibrators and reception focus positions to be focus positions of reception waves received by the plurality of vibrators and indicates the relative positions of the plurality of vibrators.

(20)
The probe unit according to (19), further including:
a transmission control unit that controls transmission timing of each vibrator; and
a reception control unit that synthesizes a reception signal from each vibrator while shifting time.

The present disclosure contains subject matter related to that disclosed in Japanese Priority Patent Application JP 2011-115880 filed in the Japan Patent Office on May 24, 2011, the entire content of which is hereby incorporated by reference.

What is claimed is:
1. A signal processing apparatus comprising:
a plurality of ultrasonic vibrators comprising a first group of at least one first ultrasonic vibrator and a second group of at least one second ultrasonic vibrator, and
a processor configured to control transmission focus positions to be focus positions of transmission waves transmitted by the plurality of ultrasonic vibrators and reception focus positions to be focus positions of reception waves received by the plurality of ultrasonic vibrators, and wherein the transmission focus positions and the reception focus positions are controlled on the basis of a change in position information regarding a position of the first group relative to the second group.

2. The signal processing apparatus according to claim 1, wherein the plurality of vibrators are divided and arranged into a plurality of probes, and the position information indicates relative positions of the plurality of probes.

3. The signal processing apparatus according to claim 2, wherein the processor controls the transmission focus positions of the transmission waves transmitted by the plurality of vibrators to be divided and arranged into the plurality of probes and the reception focus positions of the reception waves received by the plurality of vibrators to be divided and arranged into the plurality of probes on the basis of the relative positions of the plurality of probes.

4. The signal processing apparatus according to claim 1, wherein the plurality of vibrators are disposed in the probes in which the relative positions of the plurality of vibrators are changed by deformation, and the position information indicates deformation degrees of the probes.

5. The signal processing apparatus according to claim 1, wherein the processor calculates a transmission delay amount indicating a transmission delay time of each vibrator and a reception delay amount indicating a reception delay time of each vibrator on the basis of the position information.

6. The signal processing apparatus according to claim 5, further comprising:
a transmission control unit that controls transmission timing of each vibrator on the basis of the transmission delay amount; and
a reception control unit that synthesizes the reception signals from each vibrator while shifting time on the basis of the reception delay amount.

7. The signal processing apparatus according to claim 6, further comprising:
a signal processing unit that generates an ultrasonic image on the basis of a signal obtained by synthesizing the reception signals.

8. A signal processing method comprising:
controlling, using a signal processing apparatus, transmission focus positions to be focus positions of transmission waves transmitted by a plurality of ultrasonic vibrators and reception focus positions to be focus positions of reception waves received by the plurality of ultrasonic vibrators, wherein the plurality of ultrasonic vibrators comprises a first group of at least one first ultrasonic vibrator and a second group of at least one second ultrasonic vibrator, and wherein the transmission focus positions and the reception focus positions are controlled on the basis of a change in position information regarding a position of the first group relative to the second group.

9. A non-transitory computer readable medium having stored thereon instructions which, when executed by a processor, implement a method comprising:
controlling transmission focus positions to be focus positions of transmission waves transmitted by a plurality of ultrasonic vibrators and reception focus positions to be focus positions of reception waves received by the plurality of ultrasonic vibrators, wherein the plurality of ultrasonic vibrators comprises a first group of at least one first ultrasonic vibrator and a second group of at least one second ultrasonic vibrator, and wherein the transmission focus positions and the reception focus positions are controlled on the basis of a change in position information regarding a position of the first group relative to the second group.

10. A signal processing system comprising:
a plurality of ultrasonic vibrators comprising a first group of at least one first ultrasonic vibrator and a second group of at least one second ultrasonic vibrator, wherein a position of the first group relative to the second group is changeable;
a sensor that detects position information regarding the position of the first group relative to the second group; and
a processor configured to control transmission focus positions to be focus positions of transmission waves transmitted by the plurality of ultrasonic vibrators and reception focus positions to be focus positions of reception waves received by the plurality of ultrasonic vibrators, wherein the transmission focus positions and the reception focus positions are controlled on the basis of a change in the position information.

11. The signal processing system according to claim 10, wherein the plurality of vibrators are divided and arranged into a plurality of probes, and the sensor detects relative positions of the plurality of probes.

12. The signal processing system according to claim 11, wherein the processor controls the transmission focus positions of the transmission waves transmitted by the plurality of vibrators to be divided and arranged into the plurality of probes and the reception focus positions of the reception waves received by the plurality of vibrators to be divided and arranged into the plurality of probes on the basis of the relative positions of the plurality of probes.

13. The signal processing system according to claim 10, wherein the plurality of vibrators are disposed in the probes in which the relative positions of the plurality of vibrators are changed by deformation, and the sensor detects deformation degrees of the probes.

14. The signal processing system according to claim 10, wherein the processor calculates the transmission delay amount indicating a transmission delay time of each vibrator and the reception delay amount indicating a reception delay time of each vibrator on the basis of the position information, and further includes:
a transmission control unit that controls transmission timing of each vibrator on the basis of the transmission delay amount; and
a reception control unit that synthesizes the reception signals from each vibrator while shifting time on a basis of the reception delay amount.

15. The signal processing system according to claim 14, further comprising:
a signal processing unit that generates an ultrasonic image on the basis of a signal obtained by synthesizing the reception signals.

16. The signal processing system according to claim 15, further comprising:
a probe unit that includes one or more probes in which the plurality of vibrators are disposed and the sensor; and
a signal processing device that includes the signal processing unit,
wherein the processor, the transmission control unit, and the reception control unit are disposed in any one of the probe unit and the signal processing device.

17. A probe unit comprising:
a plurality of probes that include ultrasonic vibrators to be divided and arranged into the plurality of probes, wherein the plurality of probes comprises a first probe having at least one first ultrasonic vibrator and a second probe having at least one second ultrasonic vibrator; and
a sensor that detects position information regarding a position of the first group relative to the second group, wherein a change in the position information is used for controlling transmission focus positions to be focus positions of transmission waves transmitted by the plurality of vibrators and reception focus positions to be focus positions of reception waves received by the plurality of ultrasonic vibrators.

18. The probe unit according to claim 17, further comprising:
a transmission control unit that controls transmission timing of each vibrator; and
a reception control unit that synthesizes a reception signal from each vibrator while shifting time.

19. A probe unit comprising:
a probe that includes a plurality of ultrasonic vibrators comprising a first group of at least one first ultrasonic vibrator and a second group of at least one second ultrasonic vibrator of which a position of the first group relative to the second group is changed by deformation; and
a sensor that detects position information for the position of the first group relative to the second group, wherein a change in the position information is used for controlling transmission focus positions to be focus positions of transmission waves transmitted by the plurality of vibrators and reception focus positions to be focus positions of reception waves received by the plurality of ultrasonic vibrators.

20. The probe unit according to claim 19, further comprising:
a transmission control unit that controls transmission timing of each vibrator; and
a reception control unit that synthesizes a reception signal from each vibrator while shifting time.

* * * * *